United States Patent [19]
Allen et al.

[11] Patent Number: 5,468,526
[45] Date of Patent: Nov. 21, 1995

[54] MULTILAYER BARRIER FILM FOR OSTOMY APPLICATIONS

[75] Inventors: Scott I. Allen, Newark, Ohio; Duane F. Foye, Beaverton, Mich.; Michael Ferguson, Granville, Ohio

[73] Assignee: The Dow Chemical Company, Midland, Mich.

[21] Appl. No.: 123,270

[22] Filed: Sep. 20, 1993

[51] Int. Cl.⁶ .............................. B32B 27/36; B32B 7/08
[52] U.S. Cl. .................... 428/35.4; 428/35.7; 428/424.6; 428/349; 428/355; 156/244.11; 156/308.2; 156/308.4; 206/524.7; 604/332
[58] Field of Search ................... 428/35.4, 35.7, 428/213, 522, 343, 355; 156/244.11, 308.2, 308.4; 264/176.1, 177.14; 206/524.7

[56] References Cited

U.S. PATENT DOCUMENTS

| | | |
|---|---|---|
| 3,221,742 | 12/1965 | Orowan . |
| 3,725,120 | 4/1973 | Suter . |
| 3,753,828 | 8/1973 | Manne et al. . |
| 3,790,437 | 2/1974 | Haley et al. . |
| 3,801,430 | 4/1974 | Harper . |
| 3,900,616 | 8/1975 | Moore . |
| 3,934,587 | 1/1976 | Gordon . |
| 4,296,156 | 10/1981 | Lustig et al. . |
| 4,309,332 | 1/1982 | Fischer et al. . |
| 4,348,437 | 9/1982 | Lustig et al. . |
| 4,376,799 | 3/1983 | Tusim . |
| 4,410,595 | 10/1983 | Matsumoto et al. . |
| 4,485,087 | 11/1984 | Otsuka et al. . |
| 4,687,711 | 8/1987 | Vietto et al. . |
| 4,735,985 | 4/1988 | Oien . |
| 4,762,738 | 8/1988 | Keyes et al. ............... 428/36 |
| 4,772,279 | 9/1988 | Brooks et al. . |
| 4,868,024 | 9/1989 | Cross et al. . |
| 4,906,495 | 3/1990 | Martini et al. ............ 428/36.7 |
| 4,917,689 | 4/1990 | Coombes . |
| 4,946,720 | 8/1990 | Oishi et al. ............... 428/35.4 |
| 4,983,171 | 1/1991 | Schirmer ................... 604/332 |
| 5,009,648 | 4/1991 | Aronoff et al. . |
| 5,028,648 | 7/1991 | Famili et al. . |
| 5,108,382 | 4/1992 | Wright et al. . |
| 5,110,390 | 5/1992 | Martini et al. ........... 156/244.11 |
| 5,158,810 | 10/1992 | Oishi et al. ............... 428/35.4 |

FOREIGN PATENT DOCUMENTS

| | | |
|---|---|---|
| 61-241135 | 4/1985 | Japan . |
| 2083762 | 2/1985 | United Kingdom . |
| 2193925 | 7/1990 | United Kingdom . |
| 2201372 | 3/1991 | United Kingdom . |
| 2213728 | 10/1991 | United Kingdom . |

Primary Examiner—George F. Lesmes
Assistant Examiner—Helen F. Lee

[57] ABSTRACT

An oxygen and moisture impermeable multilayer barrier film is provided including a barrier layer comprising a homopolymer of vinylidene chloride or a copolymer of vinylidene chloride and vinyl chloride or methyl methacrylate. The barrier layer may be coated onto or coextruded with a water soluble film layer comprising a blend of a water soluble polymer such as polyvinyl alcohol, polycaprolactone, or polyethyloxazaline and a thermoplastic polyurethane. The multilayer film may be used for reusable or disposable ostomy bags and for heat sealable bags used in packaging agricultural chemicals, detergents, and other household chemicals.

10 Claims, 1 Drawing Sheet

MULTILAYER BARRIER FILM FOR OSTOMY APPLICATIONS

BACKGROUND OF THE INVENTION

The present invention relates to an oxygen and moisture impermeable coextruded or coated multilayer barrier film, and to articles produced therefrom including ostomy bags and heat sealable bags for packaging a variety of materials.

Plastic film laminates having oxygen and moisture vapor barrier properties are desirable for current packaging requirements, as well as for use in medical applications such as the fabrication of ostomy bags. Such films have been provided through the use of multi-ply film laminates where at least one of the plies is oxygen and moisture vapor impermeable. Typically, the films comprise chlorinated polyethylene films or plasticized polyvinyl chloride films, polyvinylidene chloride copolymer films, or multilayered structures such as ethylene vinyl acetate-polyvinylidene chloride/ethylene vinyl acetate combination films. Such constructions adequately meet the needs of oxygen and moisture barrier properties, but in use are often difficult to dispose of in a manner convenient to the user, such as by flushing the bag down a toilet.

Martini et al, U.S. Pat. No. 4,906,495, relate to a laminated film used for ostomy applications. The barrier and water soluble layers must be glued together using an additional adhesive layer. Such additional layers not only add to materials and manufacturing costs, but also result in a thicker film laminate having greater stiffness.

Both Brooks et al, U.S. Pat. No. 4,772,279, and Coombes, U.S. Pat. No. 4,917,689, relate to disposable ostomy bags having an outer water soluble layer of polyvinyl alcohol and an inner relatively insoluble layer of polyvinylidene chloride. Likewise, United Kingdom Patent Nos. 2,083,762 and 2,193,925 both show disposable ostomy bags which include a water soluble layer and a barrier layer.

However, many of the current prior art multilayer films do not have heat sealable surfaces, and thus, require complex processes for the fabrication of bags, such as positioning the barrier layer on only a portion of the film. Moreover, many require adhesives to laminate the layers so that they hold together. Accordingly, the need still exists for multilayer barrier films which may be produced by simpler and less expensive conventional processes without the need for additional adhesive layers and lamination steps and for films which are impermeable to moisture and oxygen, provide odor barrier, and which have a heat sealable surface for forming bags or the like.

SUMMARY OF THE INVENTION

The present invention meets that need by providing an oxygen and moisture impermeable multilayer barrier film which may be produced by coextrusion or coating techniques without the need for separate adhesive layers to secure the other layers together. The film provides excellent adhesion between layers, odor barrier characteristics, and a heat sealable surface for fabrication of bags.

According to one aspect of the present invention, an oxygen and moisture impermeable multilayer barrier film having a heat seal strength of at least 1.0 lb/inch of film width, and preferably greater than about 1.5 lb/inch of film width is provided. By "oxygen in permeable", it is meant that the film has an oxygen transmission rate of equal to or less than 90 cc/m$^2$/day·atm. By "moisture impermeable", it is meant that the film has a water vapor transmission rate of equal to or less than about 5 m/m$^2$/day.

In one embodiment of the invention, for use in ostomy applications, the film comprises a barrier layer of a homopolymer or copolymer of vinylidene chloride which is coextruded with or coated onto a water soluble film layer. The water soluble layer preferably comprises a blend of a water soluble polymer such as polyvinyl alcohol, polycaprolactone, or polyethyloxozaline and a thermoplastic polyurethane. Preferably, the water soluble layer is thicker than the barrier layer and comprises from about 1 to 50% by weight of the thermoplastic polyurethane, and more preferably from about 10 to 25% by weight of the thermoplastic polyurethane. The water soluble film may be a monolayer or may include two or more layers with the first layer comprising the water soluble polymer and thermoplastic polyurethane blend and the second layer comprising the same or different water soluble polymer to enhance the water solubility of the film.

Furthermore, the adhesion between the water soluble and barrier layers may be enhanced by a number of means. These include coating or coextruding a thermoplastic polyurethane layer to the water soluble layer or blending an adhesion-enhancing amount of a thermoplastic polyurethane with the barrier layer. The resulting film has an oxygen transmission rate of less than about 90 cc/m$^2$/day·atm. The barrier layer is formulated to heat seal to itself to form a disposable bag with the barrier film facing inward.

In an alternative form of this embodiment of the invention, the barrier film may further comprise an optional heat sealable skin layer of a suitable adhesive resin including such as a thermoplastic polyurethane on the side opposite the water soluble layer. Such a layer provides enhanced heat seal properties to the film.

It has been found that the multilayer barrier films of the present invention have a sufficient bond between the layers to permit coextrusion or coating without the use of additional adhesive layers and without the need for a lamination of the layers. Further, the resulting barrier film possesses properties which render the film suitable for use as disposable or reusable ostomy pouches, as well as packages for agricultural chemicals, detergents, and other household chemicals.

Accordingly, it is a feature of the present invention to provide an oxygen and moisture impermeable multilayer barrier film which may be produced using coextrusion or coating processes. Further features of the invention include odor barrier characteristics and the capability to form heat sealable bags and pouches from the film.

DETAILED DESCRIPTION OF THE PREFERRED EMBODIMENTS

The multilayer barrier film of the present invention provides greater adhesion between layers than prior art laminated films without the need for separate adhesive or glue layers and the attendant cost associated with the extra manufacturing step involved with lamination. This allows the films to be produced by a coating process in which the barrier film material is coated onto a water soluble film layer. The resulting multilayer films possess low oxygen and moisture vapor transmission rates, as well as having the odor barrier properties needed for ostomy applications. The practice of the present invention makes it possible to achieve these properties without the use of additional adhesive layers through the proper selection and blending of the components of each layer of the film.

Figure 1:
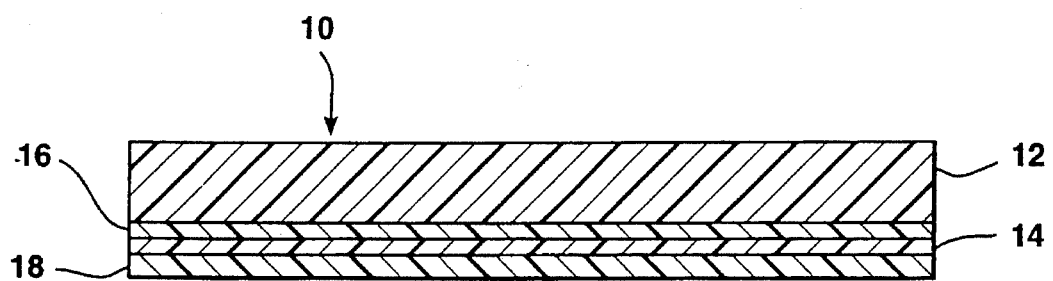
FIG. 1 is a schematic cross-section of one embodiment of the multilayer barrier film of the present invention useful as a disposable ostomy pouch including a water soluble layer.

Referring now to FIG. 1, where the layer thicknesses are not to scale, one embodiment of the invention for ostomy applications is illustrated in which multilayer film 10 comprises a barrier layer 14 of a homopolymer or copolymer of vinylidene chloride with vinyl chloride or methyl methacrylate which is coextruded with or coated onto a water soluble film layer 12. The water soluble layer 12 preferably comprises a blend of a water soluble polymer such as, for example, polyvinyl alcohol, polycaprolactone, or polyethyloxozaline and a thermoplastic polyurethane. Typically, water soluble layer 12 comprises from about 1 to 50% by weight of the thermoplastic polyurethane, and more preferably from about 10 to 25% by weight of the thermoplastic polyurethane. If desired, additional thermoplastic polyurethane may be added to the blend to enhance the adhesion of the coating to the barrier layer. However, caution must be used as the water solubility of the film is adversely affected as the amount of thermoplastic polyurethane is increased. While the water soluble film may comprise a single monolayer of the blend, it is also possible to coextrude this blend with another water soluble polymer resin to produce a bi-layer film having enhanced water solubility.

An example of a suitable barrier material includes a copolymer of vinyl chloride (15–20% by weight) and vinylidene chloride (80–85% by weight) commercially available from The Dow Chemical Company under the trademark Saran® F279. As the water soluble film layer, a water soluble polyvinyl alcohol resin such as Vinex® 5030 resin, commercially available from Air Products and Chemicals, Inc. may be used. Where a bi-layer film having enhanced water solubility is desired, other water soluble polyvinyl alcohol resins such as Vinex® 2144 may be used. The two or more layers may be coextruded. If coextruded, the relative thickness of the two layers may be controlled, giving the advantage of being able to control the water solubility characteristics of the film. For example, the unmodified water soluble polymer resin layer may comprise up to 75% or more of the bi-layer film to provide enhanced water solubility.

As previously discussed, from about 1 to 50% of a thermoplastic polyurethane may be blended with the polyvinyl alcohol or other water soluble polymer layer. Suitable thermoplastic polyurethanes include those based on the reaction of a polyisocyanate (aromatic or aliphatic) with polyester, polyether, or polycaprolactone polyols. Chain extenders such as diols and diamines may also be used in the reaction. Such thermoplastic polyurethanes are commercially available from the B. F. Goodrich Co. under the trademark Estane® and from The Dow Chemical Company under the trademark Pellethane®. A preferred thermoplastic polyurethane composition is Pellethane® 2355-95AE.

As shown, an optional thermoplastic polyurethane skin 16 may be coextruded with or coated on the surface of water soluble layer 12. Skin layer 16, and/or the thermoplastic polyurethane blended into water soluble layer 12, acts as to enhance the adhesion of barrier layer 14 to water soluble layer 12. The resulting film should have an oxygen transmission rate of less than 90 cc/m$^2$/day·atm (6 cc/100 in$^2$/day·atm). This higher oxygen transmission rate is acceptable for a barrier film which is designed to be disposable. As shown, the multilayer film may include an optional skin layer 18 of a heat sealable material such as, for example, a thermoplastic polyurethane or other suitable adhesive resin on the side of the film opposite water soluble layer 12 to provide enhanced heat seal properties for the film when folded to form a bag or pouch.

Figure 2:
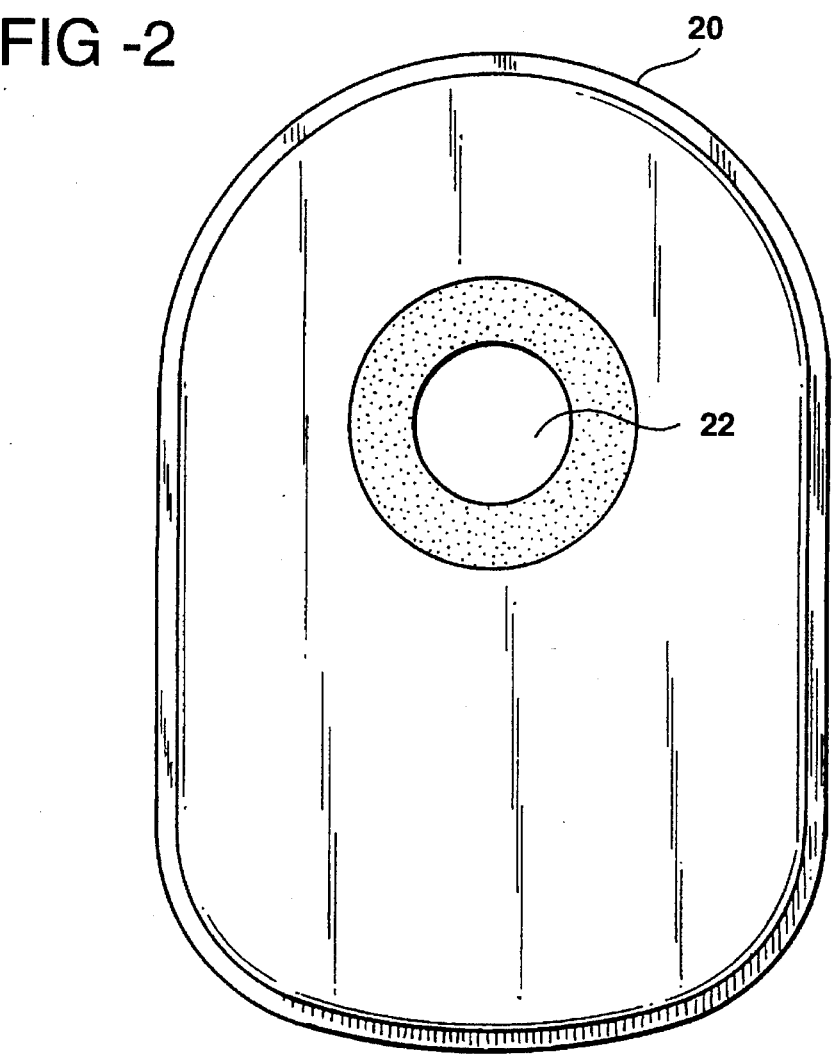
FIG. 2 is a front elevational view of an ostomy bag or pouch formed from the multilayer barrier film of FIG. 1 of the present invention.

FIG. 2 illustrates a typical disposable ostomy bag 20 including an opening 22 formed from the multilayer barrier film of FIG. 1. The bag may be formed by folding and heat sealing the edges of multilayer film 10. The film is preferably folded and sealed such that the barrier and heat sealable skin layers provide the inner surfaces of the bag or pouch 20. The barrier film of the present invention provides an easily disposable ostomy pouch with the moisture resistance and odor and oxygen barrier properties needed. As will be appreciated by those skilled in the art, the barrier films of the present invention may also find use in other packaging applications where moisture and oxygen barrier properties are required.

The multilayer film of the present invention may be produced using conventional extrusion or coating techniques. When using a coextrusion device, the configuration of the extrusion die can be varied and can be such as to reduce the thickness and dimensions of each individual layer. Thus, the thickness of the multilayer film may be controlled. Suitable coating devices include rotogravure coaters.

When coextruding a preferred embodiment of the water soluble film, advantages are obtained when the adhesion-enhancing properties of the thermoplastic polyurethane are combined with the superior water solubility properties of the polyvinyl alcohol resin. In such a coextrusion, it is preferable to make the water soluble polyvinyl alcohol layer the thicker layer, comprising 75% or more of the overall film thickness. Typically, the water soluble layer will be between about 1 to 3 mils thick, while the barrier layer will have a thickness of between about 0.1 to 0.2 mils.

However, it should be appreciated that many different layer combinations are possible, For example, the film may comprise a first layer of the water soluble polymer/thermoplastic polyurethane blend, a second layer of a thermoplastic polyurethane, and a barrier layer comprising a vinylidene chloride homopolymer or copolymer. Another possible combination comprises the water soluble polymer/thermoplastic polyurethane blend and a barrier layer comprising a vinylidene chloride/thermoplastic polyurethane blend. Still another combination is a coextruded three layer film comprising the water soluble polymer/thermoplastic polyurethane blend and a layer of thermoplastic polyurethane, and a third layer comprising the polyvinylidene chloride/thermoplastic polyurethane blend. Still another possible combination includes a first layer comprising the water soluble polymer/thermoplastic polyurethane blend, a second layer comprising thermoplastic polyurethane, a third layer of a vinylidene chloride homopolymer or copolymer, and a fourth layer of the thermoplastic polyurethane.

In order that the invention may be more readily understood, reference is made to the following examples, which are intended to be illustrative of the invention, but are not intended to be limiting in scope.

Example 1

A multilayer film was produced in accordance with the present invention by first dissolving 5% by weight of a thermoplastic polyurethane (Pellethane® 2354-80AI) tetrahydrofuran at 45°–50° C. The coating was applied to the surface of an extruded 2.0 mil thick polyvinyl alcohol film (Vinex® 5030 from Air Products and Chemicals, Inc.) containing 10% by weight thermoplastic polyurethane (Pellethane® 2355-95AE) at a coating weight of 2 gm/m$^2$, to yield a thickness of about 0.05 mil. The coated film was then placed in an oven to dry for 1½ minutes at 120° C.

A coating of the barrier material was then prepared by dissolving Saran® F279 resin in a mixture comprising 65% by weight tetrahydrofuran and 35% by weight toluene. The final lacquer contained approximately 18% by weight Saran®. The coating was applied to the surface of the coated water soluble film at a coating weight of 4 gm/m$^2$ (approximately 0.1 mil thick) and dried at 110° C. for two minutes to drive off the solvents and to crystalize the coating. The resulting multilayer barrier film had a heat seal strength of 7.7N (1.73 lb) at 300° F., 30 psi, 1 sec dwell, and an oxygen transmission rate of 13.9 cc/m$^2$/day·atm.

Example 2

A multilayer film was prepared as in Example 1 except that the water soluble film comprised 85% Vinex® 5030 and 15% Pellethane® 2355-95AE. The resulting film had a heat seal strength of 9.9N (2.22 lb) at 300° F., 30 psi, 1 sec dwell, and an oxygen transmission rate of 8.4 cc/m$^2$/day·atm.

Example 3

A multilayer film was produced in accordance with the present invention by first dissolving 5% by weight thermoplastic polyurethane (Pellethane® 2354-80AI) in tetrahydrofuran at 45°–50° C. The lacquer was applied to the surface of an extruded 2.0 mil thick polyvinyl alcohol resin (Vinex® 5030 from Air Products and Chemicals, Inc.) containing 15% by weight Pellethane® 2355-95AE resin at a coating weight of 2 gm/m$^2$, to yield a thickness of about 0.05 mil. The coated film was placed in an oven to dry for 1 ½ minutes at 120° C.

A coating of the barrier material was prepared by dissolving Saran® F279 resin and Pellethane® 2354-80AI in a mixture comprising 65% by weight tetrahydrofuran and 35% by weight toluene so that the final lacquer contained approximately 18% by weight Saran® and 5% Pellethane®. The coating was applied to the surface of the coated water soluble film at a coating weight of 4 gm/m$^2$ (approximately 0.1 mil thick) and dried at 110° C. for two minutes to drive off the solvents and crystalize the coating. The resulting film had a heat seal strength of 96.3N (1.41 lb) at 300° F., 30 psi, 1 sec dwell, and an oxygen transmission rate of 13.1 cc/m$^2$/day·atm.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A multilayer barrier film having a heat seal strength of at least about 1.0 lb/inch width of said film, said film comprising a barrier layer of a homopolymer of vinylidene chloride or a copolymer of vinylidene chloride with vinyl chloride or methyl methacrylate, said barrier layer being coextruded with or coated onto a water soluble film layer, said water soluble layer comprising a blend of a water soluble polymer and a thermoplastic polyurethane, wherein said water soluble polymer is selected from the group consisting of polyvinyl alcohol, polycaprolactone and polyethyloxozaline.

2. The multilayer barrier film of claim 1 in which said barrier layer includes blended therein or coated on the surface thereof in contact with said water soluble film layer an adhesion enhancing amount of a thermoplastic polyurethane.

3. The multilayer barrier film of claim 1 wherein said film has an oxygen transmission rate of less than about 90 cc/m$^2$/day·arm.

4. The multilayer barrier film of claim 1 wherein said barrier layer further comprises a layer of an adhesive polymer resin on the side opposite said water soluble layer.

5. The multilayer barrier film of claim 4 in which said adhesive polymer resin is a thermoplastic polyurethane.

6. The multilayer barrier film of claim 1 wherein said water soluble film layer comprises from about 1–50% by weight of said thermoplastic polyurethane.

7. The multilayer barrier film of claim 1 wherein said water soluble film layer comprises from about 10–25% by weight of said thermoplastic polyurethane.

8. The multilayer barrier film of claim 1 wherein said water soluble film layer comprises two layers, the first layer comprising said blend of a water soluble polymer and a thermoplastic polyurethane and said second layer comprising a water soluble polymer.

9. The multilayer barrier film of claim 1 wherein said water soluble layer is thicker than said barrier layer.

10. The multilayer barrier film of claim 1 wherein said moisture barrier layer and said thermoplastic polyurethane are heat sealed along their edges to form a bag or pouch.

* * * * *